US007887460B2

(12) United States Patent  (10) Patent No.: US 7,887,460 B2
Maschke  (45) Date of Patent: Feb. 15, 2011

(54) TRAINING AND THERAPY SYSTEM

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 953 days.

(21) Appl. No.: 11/408,863

(22) Filed: Apr. 21, 2006

(65) Prior Publication Data

US 2006/0259275 A1  Nov. 16, 2006

(30) Foreign Application Priority Data

Apr. 21, 2005 (DE) .................. 10 2005 018 634

(51) Int. Cl.
*A63B 71/00* (2006.01)
(52) U.S. Cl. ......................................................... 482/8
(58) Field of Classification Search ..................... 482/1, 482/2, 8, 9; 434/247; 601/36; *A63B 71/00*
See application file for complete search history.

(56) References Cited

U.S. PATENT DOCUMENTS

| 4,362,950 | A | * | 12/1982 | Turner .......................... 307/45 |
| 4,817,939 | A | * | 4/1989 | Augspurger et al. ........... 482/61 |
| 5,050,649 | A | * | 9/1991 | Kurmis ...................... 140/93 A |
| 5,812,049 | A | | 9/1998 | Uzi |
| 5,916,063 | A | * | 6/1999 | Alessandri ...................... 482/4 |
| 6,132,339 | A | | 10/2000 | Wang et al. |
| 6,260,649 | B1 | * | 7/2001 | Carney, Jr. ................... 180/220 |
| 6,656,091 | B1 | * | 12/2003 | Abelbeck et al. ................ 482/9 |
| 6,866,613 | B1 | * | 3/2005 | Brown et al. .................... 482/8 |
| 7,005,757 | B2 | * | 2/2006 | Pandian ....................... 290/1 R |
| 7,056,265 | B1 | * | 6/2006 | Shea ............................... 482/8 |

| 2003/0181290 | A1 | * | 9/2003 | Black ............................. 482/8 |
| 2005/0130741 | A1 | * | 6/2005 | Pandian ....................... 463/36 |
| 2006/0217232 | A1 | * | 9/2006 | Kondrat et al. ................. 482/3 |

FOREIGN PATENT DOCUMENTS

DE  34 25 200 A1  2/1985

(Continued)

OTHER PUBLICATIONS

B. Bjarnason-Wehrens, W. Mayer-Berger, E.R. Meister, K. Baum, R. Hambrecht, S. Gielen; "Einsatz von Kraftausdauertraining und Muskelaufbautraining in der kardiologischen Rehabilitation"; (Use of Strength Endurance Training and Muscle Development Training in Cardiological Rehabilitation); Journal of Cardiology; 2004; pp. 357-370; vol. 93, Issue 5; Steinkopff Verlag.

*Primary Examiner*—Loan Thanh
*Assistant Examiner*—Oren Ginsberg

(57) ABSTRACT

The invention relates to a training and/or therapy system for the human and/or animal body, at least consisting of: a plurality of training and/or therapy devices on which physical work is generated by means of muscular force as a function of an adjustable resistance apparatus, a computer unit by means of which all the training and/or therapy devices are networked, a plurality of reader devices on which an identification element of the patient who is doing the training or is to receive therapy can be read in, with each training and/or therapy device and the computer unit being contactable via a reader device, a data memory in which the data of the patients and their training schedules are stored; at the same time the work of setting the resistances on the adjustable resistance apparatuses of the training and/or therapy devices and the documentation during the training and/or therapy are performed automatically.

17 Claims, 3 Drawing Sheets

FOREIGN PATENT DOCUMENTS

| | | |
|---|---|---|
| DE | 42 41 336 A1 | 6/1993 |
| DE | 197 10 955 A1 | 10/1997 |
| DE | 299 11 237 U1 | 10/1999 |
| DE | 201 20 290 U1 | 10/2002 |
| DE | 298 24 810 U1 | 10/2002 |
| DE | 202 02 644 U1 | 5/2003 |
| DE | 102 20 011 A1 | 11/2003 |
| DE | 102 33 651 A1 | 4/2004 |
| DE | 102 480 35 A1 | 5/2004 |
| WO | WO 01/39089 A1 | 5/2001 |

* cited by examiner

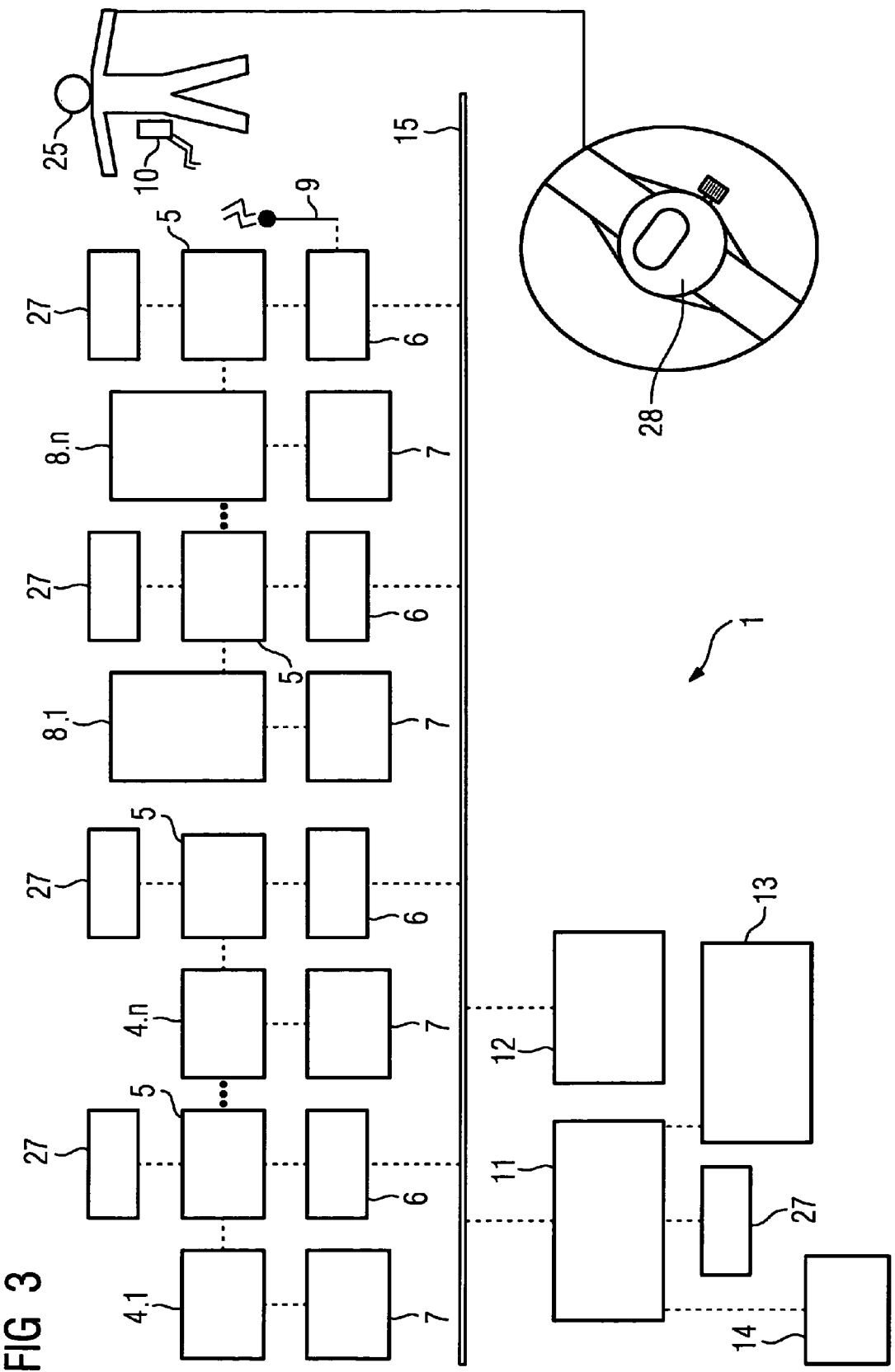

TRAINING AND THERAPY SYSTEM

CROSS REFERENCE TO RELATED APPLICATIONS

This application claims priority to the German Application No. 10 2005 018 634.3, filed Apr. 21, 2005 which is incorporated by reference herein in its entirety.

FIELD OF INVENTION

The invention relates to a training and/or therapy system for the human and/or animal body.

BACKGROUND OF INVENTION

In fitness sport, performance sport and rehabilitation it is particularly important that the physical training is performed in the correct exercise range for the patient and the sportsperson. In endurance sports, such as, for example, jogging or cycling, the pulse rate is frequently used for the purpose of improving the cardiological functions. In order to build up muscles after injuries or to support the spinal column in the case of back problems, training is generally carried out using apparatuses which counter the muscles with a resistance. In this regard reference is made to the literature "Einsatz von Kraftausdauertraining und Muskelaufbautraining in der kardiologischen Rehabilitation" ("*Use of strength endurance training and muscle development training in cardiological rehabilitation*") by B. Bjarnason-Wehrens, Zeitschrift für Kardiologie ("*Journal of Cardiology*"), Vol. 93, Issue 5, pages 357 to 370, published in 2004. In this, the training equipment is adjusted manually according to a predetermined weight setting before the respective exercise.

In the case of endurance sports the predefined frequency range can be monitored with the aid of a pulse meter. DE 42 41 336 A1 discloses a pulse meter of this kind (heartbeat rate measuring device) in which a signal transducer worn in the breast area of the sportsperson sends the determined heart rate to a display device which is located on a type of wristwatch on the sportsperson's wrist.

Various apparatuses for improving physical endurance are disclosed in DE 298 24 810 U1, DE 34 25 200 A1 and U.S. Pat. No. 6,132,339. Such apparatuses are generally termed training, sports or therapy devices, in which the human body performs work, chiefly by arm and/or leg movements under an opposing resistance. Before the start of the training, a training schedule for these apparatuses is usually prepared by the patient him-/herself or by a trainer, according to the personal data such as age, weight and physical fitness.

Analogously to the endurance training devices, in the case of the strength training devices or muscle development devices, too, several embodiment variants of which are shown by way of example in DE 102 20 011 A1, DE 299 11 237 U1 and DE 202 02 644 U1, the resistance opposing the muscle is adjusted manually, the training mostly being conducted on the basis of a training schedule. In this case the patient or sportsperson is handed the training schedule in paper form and works through the predefined training points, optionally noting the exercises performed on the paper form.

SUMMARY OF INVENTION

With individual health insurance schemes the patient receives credits or other concessions if a member of the health insurance scheme practices preventive health measures. For this purpose the visitor to a training institution or fitness studio, after performing a certain number of exercises, is issued with a certificate which is submitted to the health insurance scheme. Based on the positive health aspect and also on a certain economic interest in the use of such training equipment or training and/or therapy systems, there is also the need to improve these in terms of the hitherto very involved training adjustment and in the handling of the working through of the training points.

It is therefore an object of the invention to provide a training and/or therapy system for the human and/or the animal body which relieves the patient, the sportsperson, the therapist and the trainer of the tedious and time-consuming effort involved in adjusting the device and in addition performs the data input more efficiently and reliably.

This object is achieved by the claims.

The use of computer capacity or, as the case may be, computer-aided performance of nutrition planning and competitive sport has already proved its merit and produces improvements. In this regard reference is made to WO 01/39089 A1, from which a device is known which, with the aid of a portable computer, communicates with other computers and is used for nutrition planning. Also known, from U.S. Pat. No. 5,812,049, is an apparatus having a computing unit which can be used for time measurement for a plurality of participants in a sporting competition.

The inventor has recognized that improvements can be made possible through a targeted use and a specific application of computers in the training and therapy area for human beings and animals. The training schedules of the patient are stored on a computer unit. The computer unit is networked with the training devices and/or therapy devices. Upon entering the training center the patient is registered at reception. This takes place by means of an identification card, for example the health insurance scheme card or membership card of the training center. As a result of this registration the training schedule stored in a digital archive is loaded into the computing unit and the corresponding training parameters are transferred to the training and/or therapy devices. After completing an exercise on one training device, the patient goes to the next training device and activates this training device by introducing his or her health insurance scheme card or membership card. The already transmitted training specifications are automatically set on the training device. The number and duration of the exercises performed are recorded automatically and used to chart the training progress in the computer unit and the training schedule active therein. A computer component in the computing unit compares the achieved training targets of the individual exercises with the training schedule and from them calculates the values for a revision of the training schedule for the future training units. Ideally all the training devices are equipped with mechanical-electrical transducers and the corresponding control electronics so that it can be made possible to recover and use the mechanical muscular work output to the training and/or therapy device.

Accordingly the inventor proposes a training and/or therapy system for the human and/or animal body, at least consisting of: a plurality of training and/or therapy devices on which physical work is generated by means of muscular force as a function of an adjustable resistance apparatus, a computer unit by means of which all the training and/or therapy devices are networked, a plurality of reader devices on which an identification element of the patient who is doing the training or is to receive therapy can be read in, with each training and/or therapy device and the computer unit being contactable via a reader device, a data memory in which the data relating to the patients and their training schedules are stored, with program means and/or program modules being implemented in the computer unit by means of which the following method steps are performed: the training and/or therapy schedules for the patient are stored on the computer unit, the patient is registered at the beginning of the training and/or therapy by means of the identification element read into the reader device, by means of this registration the training schedule stored in a digital archive is loaded into the computing unit and the corresponding training parameters are transmitted to the training and/or therapy devices, the transferred training specifications and the resistance values on the adjustable resistance apparatuses are set automatically on the training and/or therapy devices, on completing an exercise on a training and/or therapy device the patient proceeds to a next training and/or therapy device and activates the training and/or therapy device by reading the identification elements into a reader device, the number and duration of the exercises performed are recorded automatically and used in order to chart the training progress in the computer unit and the training schedule active therein, a computer component in the computing unit compares the training targets achieved in the individual exercises with the training schedule and from them calculates the values for a revision of the training schedule for the future training and/or therapy units.

By this means the patient or the therapist is relieved of the tedious and time-consuming adjustment work and the task of performing the documentation during the training and/or therapy. Moreover, the data input is also performed more efficiently and reliably and the training and/or therapy is monitored and controlled more effectively.

It is advantageous if the training and/or therapy system has an interface to a further network, preferably the internet. In this way a fitness studio or therapy center, for example, can be networked with a clinical network. This enables the patient's clinical data to be taken into account during the training or therapy in the fitness studio or in the therapy center and integrated into the training or therapy.

The computer unit and the training and/or therapy devices can be networked without the use of cables. A WLAN (=Wireless Local Area Network; radio LAN), for example, is suitable for this purpose. Consequently, the computer unit and the training and/or therapy devices are not tied to specific locations when being set up and operated, since a cabling of the network is not necessary.

In order to be able to guarantee an orderly and optimal performance of the training or the therapy exercise without additional personnel resources being deployed, each training and/or therapy device should be equipped with sensors. For example, (blood) pressure measuring sensors, motion detectors, cameras and/or oxygen sensors can be used to determine additional data of the patient or his/her bodily functions during the training or therapy, which data can be used to make corrections to the further training program. If, for example, a specific value of the patient data determined by the sensors is exceeded or not attained during the predefined training sequence, in a departure from the predefined training schedule the resistance, for example, of the training and/or therapy device can be automatically adjusted or the training or therapy on this device can be stopped.

As a further optional embodiment variant, each training and/or therapy device can be equipped with a control panel and display unit. In this way the patient has the option, by means of manual or possibly voice input to the control panel, of directly influencing the setting of the training and/or therapy device. The display unit can be used, for example, to enable the patient to compare and monitor the target and actual data of the training schedule.

It is particularly favorable if the adjustable resistance apparatuses of the training and/or therapy systems have mechanical-electrical transducers and/or mechanical-thermal transducers, preferably generators. By this means the work performed or energy generated as a result of the patient's muscular effort, which was previously dissipated mostly as heat loss, can now be recovered as usable energy.

It should be pointed out at this juncture that this "energetic networking" of the training and/or therapy devices also works and can be used without the data networking of the training and/or therapy devices.

Thus, the mechanical energy can be converted into electrical or thermal energy by means of the mechanical-electrical transducers and/or the mechanical-thermal transducers and a connection to a heating and/or air conditioning system can exist for the purpose of recovering energy. In this way, as a result of the conversion of muscular work into electrical or thermal energy which is fed into the heating and/or air conditioning system, heating costs in winter and the costs of running the air conditioning system in summer are reduced.

A possible form of energy storage is provided by an arrangement in which the mechanical-electrical transducers and/or the mechanical-thermal transducers output the converted muscular work into a heat accumulator, preferably into a hot water accumulator, which buffers the energy for a relatively long period of time owing to the high thermal capacity of water, $C_{H_2O}$(at 20° C.)=4.182 kJ/kg K [=kilojoules/kilogram Kelvin].

Alternatively or in addition, the electrical voltage generated by muscular force via the mechanical-electrical transducer can be fed into the public power supply network.

In addition, an extraction unit for the room air of the training and/or therapy system can be present which converts the thermal energy stored in the room air by means of an thermal-electrical and/or a thermal-thermal transducer and feeds it into the above cited network apparatuses.

The following energy converters in particular are proposed by the inventor.

A conventional dynamo, similar to a bicycle dynamo, is suitable as a mechanical-electrical transducer. The inventor proposes heatpipes, for example, as a thermal-thermal transducer. As thermal-electrical transducers the inventor proposes thermoelements, preferably elements which use the Seebeck or Peltier effect, a physical effect of thermoelectricity. With thermoelectricity, two metals which exhibit different work functions or electron affinity for the freely movable electrons, known as Seebeck elements, are in contact. A certain thermovoltage then flows as a function of a temperature gradient. With the reverse thermoelectrical effect, the so-called Peltier effect, a temperature gradient is generated when a voltage is applied and a current flows.

The identification element of the training and/or therapy system can be an identification card, similar to a credit card or health insurance scheme card, which is read into a card reader device via mechanical contacts, preferably with pin contacts.

As an alternative to this, the identification element and the reader device can have a wireless and contactless communication link. By this means the patient can be registered more conveniently in the training and/or therapy system or on an individual training and/or therapy device, without a card having to be inserted manually into a card reader device.

In a special implementation the identification element can be embodied as an active or passive transponder, preferably as an RFID label (RFID=Radio Frequency Identification), RFID chip, RFID tag or radio label, and the reader device as a reader, preferably as a transceiver unit. In this case active transponders are usually battery-operated and can typically be read as well as written.

Active transponders are normally in the idle state, which is to say that they do not transmit any information. Only when a special activation signal is received does the transmitter activate itself. The internal memory can accommodate approximately 1 million bytes, depending on model. Compared to passive transponders, active transponders are usually larger, possess a greater transmission range, have a shorter lifespan, and are considerably more expensive.

Passive transponders draw their energy for transmitting the information from the radio waves received. The amount of stored data is significantly less than in the case of active transponders. A unique identification number is typically stored in their memory. Many passive transponders are equipped with a rewritable memory. Compared to active transponders, passive transponders are smaller and lighter, have a shorter range, a virtually unlimited service life, and are comparatively cheap.

Frequencies in the 30 to 500 kHz range or in the 10 to 15 MHz or 0.85 to 2.5 GHz range are favorable as a transmit-receive frequency for the transponder and the reader.

Systems which have a "low frequency" in the 30 to 500 kHz range have a short range and long transmission times, but are inexpensive to procure and consequently are suitable, for example, for physical access controls, immobilizers and inventory management.

Systems which have a "medium frequency" in the 10 to 15 M Hz range are suitable for short to medium ranges, a medium transmission rate and are in an affordable price category. So-called "smart labels" operate in this frequency range, usually at a frequency of 13.56 MHz.

Systems having high frequencies of 0.85 to 2.5 GHz also have a long range (approx. 30 meters) and a fast reading speed, but the purchase prices increase rapidly for higher-performance systems. Systems in this class are used, for example, in the automated toll systems sector and in freight car detection.

If a wireless transponder technology of this kind is used, the transponder can be attached to or integrated with the patient's body. Items suitable for this purpose are preferably articles of (sports) clothing, shoes or objects such as watches, a mobile radio device or jewelry which the patient carries about his/her person during the sporting activity or therapy.

It is favorable if the identification element has a writable memory in which the training schedule of the patient and/or the energy value s achieved by the patient are stored in addition to personal data. For example, the energy values which the patient has achieved by muscular work and which are stored on the identification element can serve as proof of sporting activity for the health insurance scheme. As already explained in the introductory remarks, the patient receives credits or other concessions if a member of a health insurance scheme takes preventive health measures. In contrast to a pure listing of the number of visits to the fitness studio or therapy center, which do not, however, provide an insight into the extent to which the patient was sportingly active or even whether the patient was sportingly active at all, an accurate check on the activity or activities of the patient is possible in this case.

BRIEF DESCRIPTION OF THE DRAWINGS

The invention is explained in more detail below with reference to exemplary embodiments illustrated in the drawing.

It is pointed out in this context that only the elements essential to the immediate understanding of the invention are shown. The figures show.

DETAILED DESCRIPTION OF INVENTION

Figure 1:
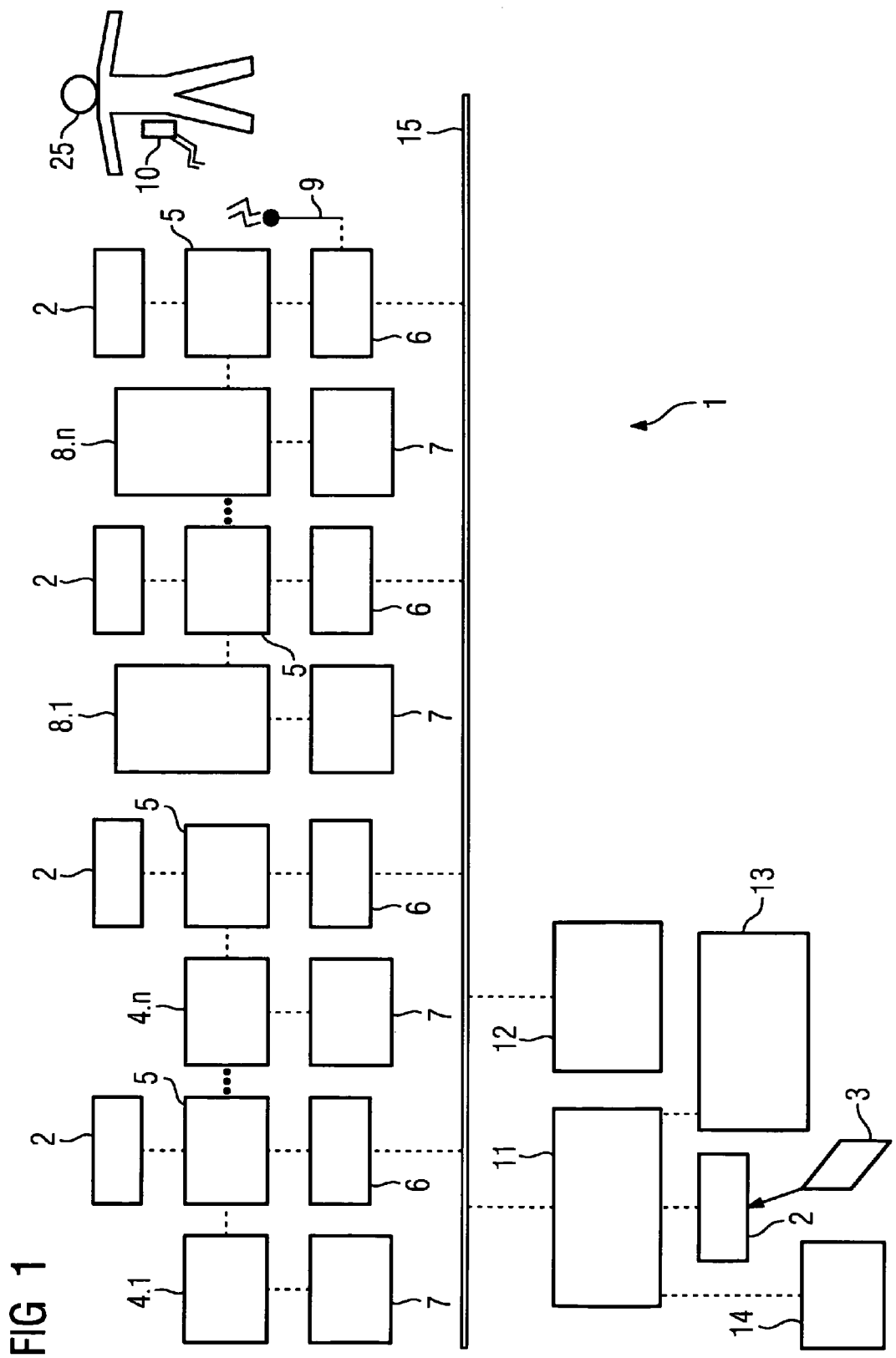
FIG. 1 a schematic representation of a training and/or therapy system for automatic control of the training, FIG. 2 a schematic representation of a training and/or therapy system with energy recovery, and FIG. 3 a schematic representation of a training and/or therapy system for automatic control of the training with wireless patient registration.

FIG. 1 shows a schematic representation of a training and/or therapy system for automatic training control 1. Such a training and/or therapy system for automatic training control 1 can be a specially equipped fitness studio or a therapy center for physical rehabilitation. Within the training and/or therapy system 1 there are disposed a plurality of internetworked training devices, in this case, by way of example, n endurance training devices 4.1 to 4.n and n strength training devices 8.1 to 8.n on which a patient 25 or sportsperson can train as desired or according to a training schedule. One aspect of the invention is to automate the training or therapy such that resistances/weights on the devices no longer need to be adjusted individually by the trainer, therapist or person doing the training, the working through of the training schedule is simplified, and in addition the (training) data input can be performed more efficiently and reliably. For this purpose the training devices 4.1 to 4.n and 8.1 to 8.n are connected to a central computer 11 via data processors 6 and a (data) network 15. Various data relating to the patient 25, such as training schedule, weight settings, (maximum) duration of the training, etc., can be stored in a data archive 13 likewise connected to the computer 11. The (data) network 15 of the training and/or therapy system for automatic training control 1 can be connected to further networks, such as, for example, the internet 14 or a clinical intranet, in order to enable additional data to be integrated during the training exercise.

At the beginning of the training or therapy, the patient 25 introduces an identification card 3, for example a health insurance scheme card or a membership card, into a card reader 2 at the central computer 11, as a result of which the person of the patient 25 is registered. Following identification of the patient 25, a training schedule stored for the patient in the data archive 13 is activated automatically or, in the case of a new patient, the system prompts for a new training schedule to be created/input.

If the patient 25 starts the training or therapy on an endurance training device 4.1 to 4.n or on a strength training device 8.1 to 8.n, either an identification card 3 is inserted into a card reader device on this device also or, alternatively, the patient 25 can perform an identification via a user I/O 5 or via the device's control panel. Depending on the individual training schedule of the patient 25, the resistance value is set on this device, in this implementation by way of mechanical-electrical transducers 7. A data processor on each training device 4.1 to 4.n or 8.1 to 8.n can process the current training data and forward it via the (data) network 15 to the central computer 11 or to the monitoring unit 12.

The training is supervised with regard to training limit values by means of a monitoring unit 12. In this arrangement bodily functions of the patient 25 can be monitored for example via a patient sensor 10 which is connected to the (data) network 15 via an interface 9. Once the training on this device has been completed, the training and/or therapy system for automatic training control 1 signals the end of training via a display unit 5 of the user I/O and prompts the patient to switch to the next device.

Analogously to the start of the training on the first device, the patient 25 is registered by means of the identification card or an input on the second training device, as a result of which the resistance or weight is set and adjusted automatically.

Figure 2:
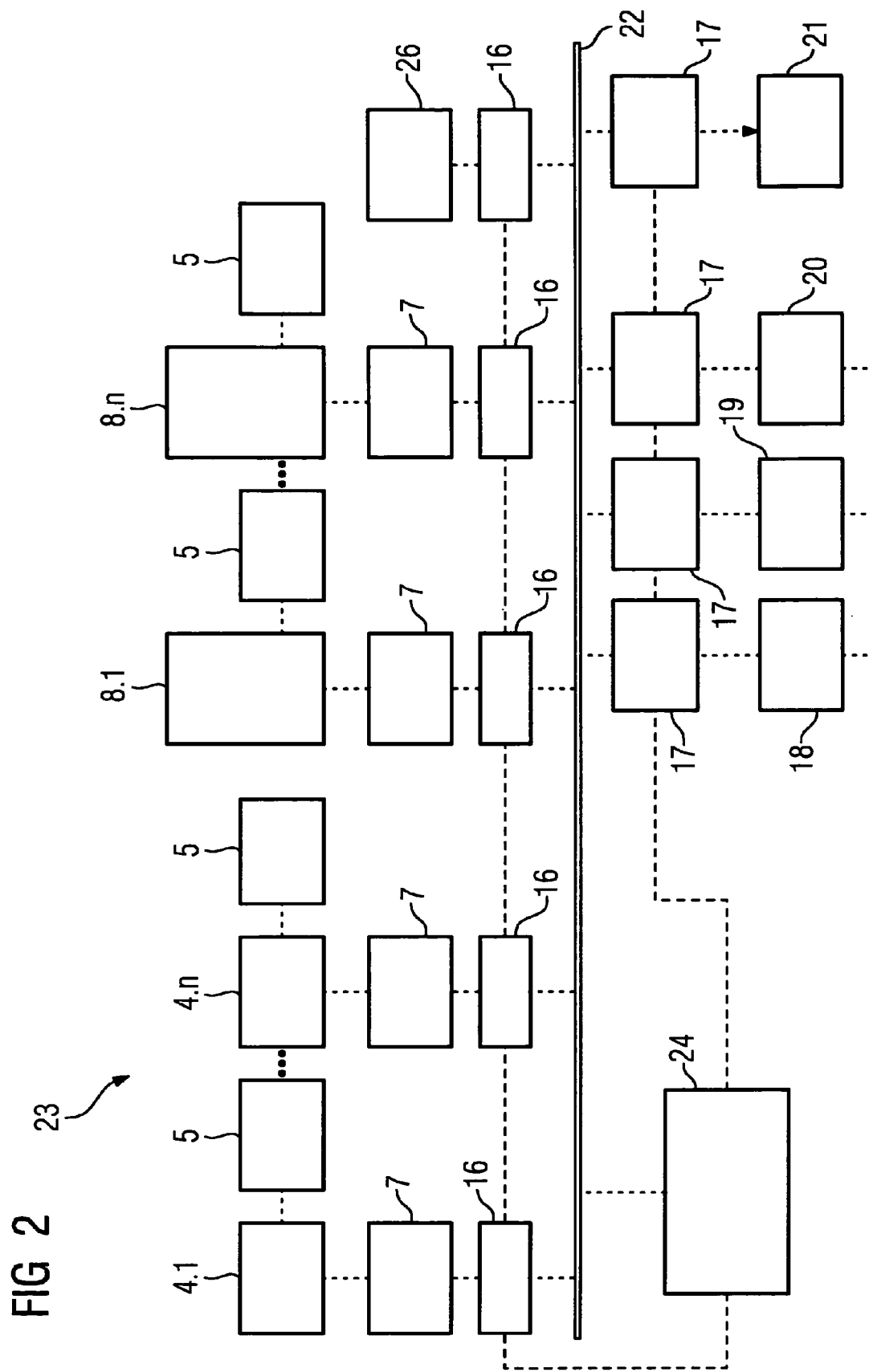

FIG. 2 shows a schematic representation of a training and/or therapy system with energy recovery 23. For the sake of clarity, the (data) network from FIG. 1 has not been shown in FIG. 2. In an analogous manner to the data networking of the individual training devices 4.1 to 4.n or 8.1 to 8.n in FIG. 1, in the implementation of the training and/or therapy system the training devices 4.1 to 4.n or 8.1 to 8.n from FIG. 2 are linked to an (energy) network 22. In this arrangement the muscular work output to the training devices 4.1 to 4.n or 8.1 to 8.n is to be converted into reusable energy and initially fed into the (energy) network 22.

In this case the muscular work output to the training devices 4.1 to 4.n or 8.1 to 8.n is converted via mechanical-electrical transducers 7, for example dynamos, into electrical voltages. The voltage values are fed into the (energy) network 22 via voltage regulators 16 and adjusted by a control and regulation unit 24. The current flowing as a result of the generated voltage can be fed into the public power supply network 21 and remunerated in a similar manner to the solar cell current. Alternatively, the current can be converted into other diverse forms of energy, for example thermal energy, via energy converters 17, such as thermal-thermal or thermal-electrical transducers, and used in a heating and/or air conditioning system 19 or for producing hot water 20. The current can also be supplied to an energy accumulator 18 or an energy converter 26 for the room air.

FIG. 3 shows a schematic representation of a training and/or therapy system 1 for automatic training control with wireless patient registration. In contrast to the training and/or therapy system 1 from FIG. 1, in which the patient 25 introduces his/her identification card more or less mechanically into a reader device, in FIG. 3 the patient is registered upon entering the fitness studio or therapy center and at the start of the training on a training and/or therapy device 4.1 to 4.n and/or 8.1 to 8.n via a wireless connection of the identification element to the reader device. In this embodiment the identification element is integrated in a watch 28 on the arm of the patient as an RFID module. This RFID module is in contact with an RFID transceiver 27.

In principle it is also possible to integrate the patient sensor 10, which measures, for example, pulse, blood pressure or (blood) oxygen saturation, in the watch 28.

It goes without saying that the above cited features of the invention can be used not only in the combination specified in each case, but also in other combinations or in isolation, without departing from the scope of the invention.

All in all, the training and/or therapy system according to the invention makes available a system which relieves a living thing, the patient, the sportsperson, the therapist and the trainer, of the tedious and time-consuming work of adjusting the devices and in addition performs the data input more efficiently and reliably. In a special embodiment of the training and/or therapy system it is even made possible to recover the energy which the person doing the training inputs into the training devices and which in the past remained unused.

The invention claimed is:

1. A training and therapy system for a human or animal body, comprising:
   a plurality of training or therapy devices on which physical work is generated using muscular force, the physical work dependent on an adjustable resistance apparatuses;
   a computer unit for networking the training or therapy devices;
   an identification element;
   a plurality of reader devices for reading the identification element of a patient under training or therapy, each training or therapy devices and the computer unit configured to be contacted via the respective reader device;
   a data memory connected to the computer unit for storing data related to a plurality of patients and to a plurality of training or therapy schedules of the plurality of patients; and
   a software program implemented on the computer unit, the software program configured to:
   store in the computer unit a training or therapy schedule of the patient under training or therapy;
   read the identification element by at least one of the reader devices for a registration of the patient under training or therapy when starting the training or therapy starts;
   retrieve the stored training or therapy schedule from the computer based upon the registration;
   transmit training parameters to the plurality of training or therapy devices based upon the retrieved training or therapy schedule;
   automatically adjust the training or therapy devices and the resistance apparatuses based upon the transmitted training parameters;
   enable starting workout at a first of the training or therapy devices, by the patient under training or therapy;
   enable proceeding to a second of the training or therapy devices upon completing an exercise on the first training or therapy device;
   activate the second training or therapy device by reading the identification element by the respective reader device;
   record at least a number and a duration of all exercises performed on any training or therapy device by the patient under training or therapy;
   determine training or therapy progress from the recorded number and duration of the exercises;
   save the determined training or therapy progress in the retrieved training or therapy schedule; and
   determine an updated training or therapy schedule for the patient under training or therapy using the training or therapy progress,
   wherein the identification element includes a writable memory for storing the training schedule of the patient under training or therapy or for storing energy values generated by the patient under training or therapy.

2. The system according to claim 1, wherein the updated training or therapy schedule is determined by comparing individual training targets achieved in individual exercises to corresponding training targets included in the retrieved training or therapy schedule.

3. The system according to claim 1, wherein the updated training or therapy schedule includes updated training parameters or updated settings for the resistance apparatuses.

4. The system as claimed in claim 1, wherein the computer unit comprises an interface to a further network.

5. The system as claimed in claim 4, wherein the further network is an intranet or the internet.

6. The system as claimed in claim 1, wherein the system embodies a wireless network.

7. The system as claimed in claim 6, wherein the wireless network is a WLAN or Bluetooth network.

8. The system as claimed in claim 1, wherein each training or therapy device comprises a sensor for acquiring a measuring value related to the patient under training or therapy.

9. The system as claimed in claim 8, wherein the sensor is selected from the group consisting of a blood pressure sensor, a motion detector, a camera and a sensor for measuring an oxygen content of the blood of the patient under training or therapy.

10. The system as claimed in claim 1, wherein each training or therapy device comprises a control panel and a display unit.

11. The system as claimed in claim 1, wherein usable energy is fed into a heating system, an air conditioning system, an energy accumulator, a public power supply network or back into at least one component of the system.

12. The system as claimed in claims 1, wherein the identification element is an identification card configured to be inserted into and read by the reader devices.

13. The system as claimed in claim 1, wherein the identification element and the reader device communicate wirelessly.

14. The system as claimed in claim 13, wherein the identification element is an active or passive transponder.

15. The system as claimed in claim 14, wherein the identification element is selected from the group consisting of an RFID label, an RFID chip, an RFID tag and a radio label.

16. The system as claimed in claim 13, wherein the wireless communication is established within a transmit and receive frequency range selected from the group consisting of a range between 30 kHz and 500 kHz, a range between 10 MHz and 15 MHz and a range between 0.85 GHz and 2.5 GHz.

17. The system as claimed in claim 14, wherein the transponder is attachable to the body of the patient under training or therapy.

* * * * *